United States Patent
Yi et al.

(10) Patent No.: US 8,853,417 B2
(45) Date of Patent: Oct. 7, 2014

(54) NON-HALOGEN ACTIVATING AGENT USED AS FLUX

(75) Inventors: Zongming Yi, Changde (CN); Yi Liu, Foshan (CN)

(73) Assignee: Hunan Astar Biotechnology Ltd., Changde (CN)

( * ) Notice: Subject to any disclaimer, the term of this patent is extended or adjusted under 35 U.S.C. 154(b) by 0 days.

(21) Appl. No.: 13/389,439

(22) PCT Filed: Mar. 8, 2010

(86) PCT No.: PCT/CN2010/000285
§ 371 (c)(1),
(2), (4) Date: Feb. 7, 2012

(87) PCT Pub. No.: WO2011/066706
PCT Pub. Date: Jun. 9, 2011

(65) Prior Publication Data
US 2012/0142938 A1 Jun. 7, 2012

(30) Foreign Application Priority Data

Dec. 3, 2009 (CN) .......................... 2009 1 0227146

(51) Int. Cl.
| | | |
|---|---|---|
| *C07D 233/54* | (2006.01) | |
| *C07C 309/04* | (2006.01) | |
| *B23K 35/22* | (2006.01) | |
| *C07C 309/06* | (2006.01) | |
| *B23K 35/362* | (2006.01) | |
| *C07C 309/08* | (2006.01) | |
| *B23K 35/36* | (2006.01) | |
| *B23K 35/24* | (2006.01) | |
| *C07C 309/05* | (2006.01) | |

(52) U.S. Cl.
CPC ............... *C07C 309/04* (2013.01); *B23K 35/22* (2013.01); *C07C 309/06* (2013.01); *B23K 35/362* (2013.01); *C07C 309/08* (2013.01); *B23K 35/36* (2013.01); *B23K 35/24* (2013.01); *C07C 309/05* (2013.01)
USPC ...................................................... 548/335.1

(58) Field of Classification Search
USPC ...................................................... 548/335.1
See application file for complete search history.

(56) References Cited

U.S. PATENT DOCUMENTS

| | | | |
|---|---|---|---|
| 5,507,882 | A | 4/1996 | Bristol et al. |
| 7,566,788 | B2 | 7/2009 | Bohlin |
| 2005/0107440 | A1 | 5/2005 | Ho et al. |
| 2007/0155769 | A1 | 7/2007 | Pujol et al. |
| 2007/0225346 | A1 | 9/2007 | Bohlin |
| 2008/0281105 | A1 | 11/2008 | Macdonald et al. |
| 2010/0022610 | A1 | 1/2010 | Bohlin |

FOREIGN PATENT DOCUMENTS

| | | | |
|---|---|---|---|
| CN | 1129213 | A | 8/1996 |
| CN | 1209374 | A | 3/1999 |
| CN | 1398698 | A | 2/2003 |
| CN | 1419539 | A | 5/2003 |
| CN | 1471450 | A | 1/2004 |
| CN | 1612874 | A | 5/2005 |
| CN | 1913891 | A | 2/2007 |
| CN | 101106992 | A | 1/2008 |
| CN | 101389623 | A | 3/2009 |
| CN | 101454293 | A | 6/2009 |
| CN | 101543943 | A | 9/2009 |
| CN | 101564805 | A | 10/2009 |
| CN | 101569966 | A | 11/2009 |
| CN | 101575330 | A | 11/2009 |
| JP | 7136794 | A | 5/1995 |
| WO | 0172703 | A1 | 10/2001 |
| WO | 2007100282 | A1 | 9/2007 |

OTHER PUBLICATIONS

International Search Report in international application No. PCT/CN2010/000285, mailed on Sep. 9, 2010.
English Translation of the Written Opinion of the International Search Authority in international application No. PCT/CN2010/000285, mailed on Sep. 9, 2010.

*Primary Examiner* — Rebecca Anderson
(74) *Attorney, Agent, or Firm* — Oppedahl Patent Law Firm LLC

(57) ABSTRACT

A non-halogen active agent for a flux is a sulfonate formed by a sulfonic acid reacting with an organic base. The sulfonic acid can be an alkyl sulfonic acid, alkyl disulfonic acid, hydroxyl sulfonic acid or halogenated sulfonic acid. The organic base can be an organic amine, carbamidine, imidazole, phosphorus. The non-halogen active agent for a flux has the advantage of high activity and low corrosion.

1 Claim, No Drawings

NON-HALOGEN ACTIVATING AGENT USED AS FLUX

TECHNICAL FIELD

The present disclosure relates to a flux used in soldering in electronic industry, and in particular to an active component in the flux, namely a non-halogen active agent for the flux.

BACKGROUND

In a brazing process, a flux is an indispensable material which plays a very important role. The most crucial part in the flux is active components. An active agent in the flux is mainly used to remove an oxide film on the surface of a substrate to reduce a surface tension during soldering, increase wettability of the metal of solder and a soldering pad, thereby improving solderability.

The requirements for an ideal active agent are as follows: in general cases, the active agent is stable, and does not react with a substrate even being in contact with the substrate; during the course of using, when heated up to a certain temperature, the active material starts to melt and wet the solder and the soldering pad; with a further increase of the temperature, the active material starts to gradually release its activating capability; when reaching the optimum soldering temperature, all the activating capability is released; after completion of soldering, with a decrease of the temperature, the remaining active material returns to an original inert state; in the course of soldering, salts such as copper salt, tin salt and other salts, generated through reacting with an oxide film, should not influence electrical performance; of course, should not corrode the substrate.

Generally, a current active agent may be an inorganic acid salt of organic substances, or an organic acid, or mixtures thereof. Most commonly used inorganic acid salts are halogen acid salts, such as amine hydrochlorides, guanidine hydrochlorides, amine hydrobromides, guanidine hydrobromides, etc. All of them have a characteristic of high activity. However, their defects are fatal: corroding the substrate and severely influencing the electrical performance. The active agent of organic acids is currently a development hotspot, with continuous appearance of patents, such as those disclosed in U.S. Pat. No. 5,507,882, 1996 ("Bristol Samuel V Low residue water-based soldering flux and process for soldering with same"), Pat. CN1209374A, 1999 (Shengbo LI, "No-clean flux with low solid content"), Pat. CN1398698A, 2003 (Hesheng DENG et al, "No-clean liquid flux"), Pat. CN1011564805A, 2009 (Yongping LEI et al, "Novel environment-friendly flux for SnAgCu lead-free soldering paste with low Ag content). Generally, an organic carboxylic acid, especially dicarboxylic acid such as butane diacid, pentane diacid and hexane diacid, is preferably used to solve the problem of corrosion in using halogen active agents and the problem of electrical performance generated therefrom. Indeed, the problem is solved. Unfortunately, the activity is greatly reduced, which is not comparable with the activity of halogen active agents at all. The compromised solution is as follows: combining the organic acid and halogen and finding a balance between the corrosion and activity, such as those disclosed in Pat. CN101543943A, 2009 (Junhu QIN et al, "No-clean lead-free rosin-core flux with low halogen content and preparation method thereof"), Pat. CN101569966A, 2009 (Jian WU et al, "A lead-free solder paste and method for preparing its flux") etc. The solution can only be applied to a variety with low performance requirements, but not to a variety with high performance requirements.

SUMMARY

The purpose of the present disclosure is to provide a substance, which has no corrosion to a metal substrate and metal solder but has high reaction activity with a metal oxide formed therefrom. Use of the substance as an active agent brings both high activity as using a halogen active agent and low corrosion as using an organic acid.

The present disclosure is realized as follows: a non-halogen active agent for a flux is a sulfonate formed by a sulfonic acid reacting with an organic base. In general cases, the salt is quite stable, which would not react with the metal substrate, the solder and the metal oxide formed therefrom. Upon reaching a soldering temperature, free sulfonic acid is decomposed from the sulfonate and the activity is released. After completion of the soldering, with a decrease of the temperature, the remaining sulfonic acid is recombined with the organic base to form the inert sulfonate.

The sulfonic acid of the sulfonate of the present disclosure may have the following general formula:

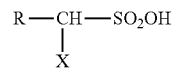

wherein, R may be an alkyl, phenyl or hydrogen atom; X may be a halogen atom, sulfonic group, hydroxyl or hydrogen atom.

The sulfonic acid may be an alkyl sulfonic acid, alkyl disulfonic acid, hydroxyl sulfonic acid or halogenated sulfonic acid, such as a methane sulfonic acid, ethane sulfonic acid, propane sulfonic acid, methane disulfonic acid, ethane disulfonic acid, propane disulfonic acid, ethylenehydrinsulfonic acid, benzene sulfonic acid, p-toluenesulfonic acid, chloromethanesulfonic acid and the like.

The sulfonic acid may be preferably the alkyl disulfonic acid, such as methane disulfonic acid, ethane disulfonic acid and propane disulfonic acid.

The sulfonic acid may be most preferably the methane disulfonic acid, having the following structural formula:

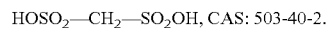

The sulfonate of the present disclosure may be triethylamine methane disulfonate, diphenyl guanidine methane disulfonate, diisobutylamine methane disulfonate, diphenylamine methane disulfonate, triethanolamine methane disulfonate, N-methylimidazole methane disulfonate, pyridine methane disulfonate, lauryl amine methane disulfonate, octadecyl amine methane disulfonate, potassium methane disulfonate, sodium methane disulfonate, copper methane disulfonate, stannous methane disulfonate or the like.

The sulfonate of the present disclosure as an active agent in the flux may be used independently or be combined with other active agents for use.

The sulfonate of the present disclosure is impossible to be present in a flux, unless it is added intentionally; based on this, we claim that only if a sulfonic group is detected by ion chromatography, it is determined that the substance of the disclosure has been used.

The organic base of the present disclosure may be selected from a wide range. It may be selected from organic amines, guanidines, imidazoles, phosphorus etc., which is used to form salt with the sulfonic acid, and is of no activity under non-soldering conditions.

Advantages of the Present Disclosure

1. High activity: the active agent of the present disclosure, when in the active state, is a strong acidic substance, with acid strength close to hydrohalogen acid and activity comparable to a halogen active agent;
2. Low corrosion: the active agent of the present disclosure, when under the non-soldering conditions, has no corrosion to the metal of the soldering pad and the solder, having the advantage of low corrosion as using an organic acid active agent; and
3. Wide range of applications: the active agent of the present disclosure solves the problem of high corrosion of traditional halogen active agents and overcomes the defect of low activity of organic acid active agents in the prior art; the active agent of the present disclosure can be used as an active component in various kinds of fluxes to prepare various kinds of halogen-free fluxes with high performance, such as no-clean solvent-based flux, water soluble flux, no-clean water soluble flux, to be applied in soldering techniques with different requirements, including not only lead soldering but also lead-free soldering.

DETAILED DESCRIPTION

Following embodiments are provided to further describe the present disclosure. Of course, the present disclosure is not limited to these embodiments.

Embodiment 1: Application In No-clean Liquid Flux

The formulation by weight is as follows: 95% of isopropanol, 3% of diethylene glycol monomethyl ether, 1.5% of butane diacid, and 0.5% of diphenyl guanidine methane disulfonate. The above substances are stirred to be dissolved, so as to obtain a colorless transparent liquid flux. At the temperature of 250° C., the flux can be fast spread on a molten metal surface of an alloy containing 99.3% of tin and 0.7% of copper to quickly react with tin-copper oxides on the molten surface, so as to realize good fluxing effects. At room temperature, the flux does not chemically corrode the cooper and tin substrate. On a wave-soldering production line, after an electrical product is tin soldered, insulation resistance on the surface of a PCB plate is above $1 \times 10^{13} \Omega$, showing good electrical performance.

Embodiment 2: Application In Solid Flux Contained In Tin Wires

The formulation by weight is as follows: 95% of rosin, 3% of ethylene glycol monophenyl ether, 2% of imidazole methane disulfonate. The above substances are heated to be melted and completely dispersed, so as to obtain a transparent light yellow solid flux. In the production of tin wires, the content of the flux which is squeezed and pressed on the tin wires is controlled between 2.8% to 3.0%, and the tin wires used are alloy containing 99.3% of Sn and 0.7% of Cu. The manufactured tin wires have good wettability on copper foils, bright soldering spots and transparent remnants. In the course of using, there is no smell, no rosin spattering, and the effect of the flux is good, and insulation resistance of the remnants of tin wires is above $1 \times 10^{13} \Omega$.

Embodiment 3: Application In Soldering Paste

The formulation by weight is as follows: 50% of rosin, 40% of diethylene glycol monobutyl ether, 5% of stearic amide, 5% of guanidine methane disulfonate. The above substances are heated to be melted and completely dispersed, so as to obtain a translucent light yellow pasty flux. Tin powder containing metal components which are 96.5% of Sn, 3.0% of Ag and 0.5% of Cu is used, and the diameter of the tin powder is between 25 and 45 microns. 90% of the tin powder and 10% of the flux are mutually mixed and dissolved to obtain a tin paste. The tin paste has good printing effects, and full and bright soldering spots can be obtained on soldering pads of copper, tin and nickel substrates through heating. Insulation resistance of the remnants at soldering spots is up to $1 \times 10^{13} \Omega$, and the soldering spots will not be corroded and get black after six months at room temperature.

The invention claimed is:

1. A non-halogen active agent for a flux, being imidazole methane disulfonate.

* * * * *